(12) United States Patent
Chen

(10) Patent No.: US 7,029,701 B2
(45) Date of Patent: *Apr. 18, 2006

(54) COMPOSITION FOR THE TREATMENT AND PREVENTION OF ISCHEMIC EVENTS

(75) Inventor: Chih-Ming Chen, Davie, FL (US)

(73) Assignee: Andrx Pharmaceuticals, LLC, Davie, FL (US)

( * ) Notice: Subject to any disclaimer, the term of this patent is extended or adjusted under 35 U.S.C. 154(b) by 7 days.

This patent is subject to a terminal disclaimer.

(21) Appl. No.: 09/950,536

(22) Filed: Sep. 10, 2001

(65) Prior Publication Data

US 2002/0051814 A1   May 2, 2002

Related U.S. Application Data

(60) Provisional application No. 60/231,618, filed on Sep. 11, 2000.

(51) Int. Cl.
*A61K 9/14* (2006.01)
*A61K 9/16* (2006.01)
*A61K 9/20* (2006.01)
*A61K 9/22* (2006.01)
*A61K 9/48* (2006.01)

(52) U.S. Cl. .................. 424/489; 424/451; 424/457; 424/464; 424/468; 424/490; 514/960; 514/964

(58) Field of Classification Search ............... 424/400, 424/464, 465, 466, 468, 469, 470, 472, 474, 424/476, 480, 484, 489, 490, 494, 451, 452, 424/495; 514/338, 951, 960, 962, 964; 560/143
See application file for complete search history.

(56) References Cited

U.S. PATENT DOCUMENTS 6,365,184 B1 * 4/2002 Depui et al. ................ 424/469
6,605,303 B1 * 8/2003 Karehill et al. ............. 424/484
6,610,323 B1 * 8/2003 Lundberg et al. ........... 424/458

* cited by examiner

*Primary Examiner*—Sreeni Padmanabhan
*Assistant Examiner*—S. Gollamudi
(74) *Attorney, Agent, or Firm*—Davidson, Davidson & Kappel, LLC

(57) ABSTRACT

The invention relates to pharmaceutical compositions comprising omeprazole and aspirin wherein the combination is useful for the treatment and prevention of cardiovascular events including heart attacks and platelet aggregation leading to a potential cardiac event. A variety of drug delivery systems may be utilized to deliver the combination of active ingredients. The preferred delivery system utilizes a tablet or capsule containing an inert sugar core particle that is coated with subparticles of a coated omeprazole wherein the coating contains omeprazole, a binder, a surface active agent and a basifying agent along with a filler. The aspirin may be combined with this formulation to coat the sugar sphere or it may be part of a separate coating composition that forms a multilayer system that is ultimately coated with an enteric coating and then formed into the tablet or capsule by conventional means.

16 Claims, No Drawings

COMPOSITION FOR THE TREATMENT AND PREVENTION OF ISCHEMIC EVENTS

This application claimes the benefit of Provisional Application No. 60/231,618 filed Sep. 11, 2000.

BACKGROUND OF THE INVENTION

Non-narcotic analgesics including aspirin are known to be effective in relieving pain and inflammation associated with the production or presence of prostaglandins. In addition to its pain relieving or inflammation relieving properties, aspirin or acetylsalicyclic acid is also known to cause irritation and ulceration of the stomach and duodenum at the doses necessary to relieve pain and inflammation. Because of this, numerous delivery systems for aspirin have been developed that buffer or reduce the ulcerative effects of aspirin.

It is also known that aspirin has significant anti-coagulant or anti-clotting properties that can reduce the risk of heart attack or related ischemic events (i.e., as a prophylactic) or it can be used during a heart attack to reduce further damage or death. When prescribed for chronic use, the dose of aspirin that is generally recommended is far less (e.g. 50–150 mgs once per day) than the dosage that is generally necessary to relieve pain and inflammation (500–650 mgs per dose as needed). The chronic administration or use of aspirin at higher doses is not generally recommended because of the potential for ulcerative bleeding.

A variety of medications have also been developed and marketed to treat and/or prevent conditions, diseases or disorders of the gastrointestinal tract. Some of the most common medications include the antacids and the anti-ulcer drugs that are sold over the counter and through prescriptions. The most commonly prescribed medication that inhibits gastric acid secretion is the compound omeprazole and that is sold under the tradename PRILOSEC®. It is known that this compound is rapidly degraded under acidic conditions.

It has surprisingly been found that the combination of the acidic acetylsalicyclic acid (aspirin) and omeprazole in a single dosage form or delivery vehicle for oral administration is useful for the treatment and prevention of heart attacks and the reduction of potential thrombotic events. This combination may be delivered without the expected degradation of the acid labile omeprazole and can include higher doses of aspirin (greater than 150 mgs) than is normally prescribed for the treatment and/or prevention of heart attacks. The combination of aspirin and omeprazole provides sufficient anti-coagulant activity while also providing a gastric acid inhibiting effect to permit delivery of higher doses of aspirin, although low doses of aspirin along with the normally recommend dose of omeprazole (10, 20, or 40 mgs QD) may also be delivered. In addition, the present invention comprises pharmaceutical compositions comprising aspirin, omeprazole and other active ingredients including, for example, citric acid and/or antioxidant agents.

SUMMARY OF THE INVENTION

The present invention comprises or consists essentially of a pharmaceutical composition comprising aspirin and the compound omeprazole or its pharmaceutically acceptable salt (acid or base). In addition, the invention comprises a method of treating or preventing heart attack or associated thrombotic events comprising administering a pharmaceutically effective amount of a composition comprising aspirin and omeprazole in a single delivery vehicle or dosage form.

The preferred delivery vehicle or dosage form is a controlled releases medication comprising the active ingredients aspirin and omeprazole. The controlled release medication may be selected from a multitude of known delivery vehicles or systems including osmotic delivery, multi-layered delivery, bead or particle delivery and can be formulated in tablets or capsules.

In one embodiment the present invention is directed to a controlled release dosage form which comprises:

(a) a homogeneous compressed core that comprises a compressed granulation of:
  (i) particles of aspirin coated with an enteric polymer that are dispersed onto a solid pharmaceutical filler and
  (ii) particles of omeprazole that are uncoated or coated with an enteric polymer that are dispersed onto a solid pharmaceutical filler; and
(b) a continuous compressed outer layer around said homogeneous compressed core that comprises a compressed granulation of:
  (i) one or more pharmaceutically acceptable polymers that form a hydrogel and that may additionally comprise aspirin and omeprazole. Delivery systems similar to this have been described in U.S. Pat. No. 5,922,353 which is hereby incorporated by reference.

In another embodiment, the present invention comprises a controlled release dosage form which comprises:

(a) a compressed tablet core which contains a coated aspirin and omeprazole, a pharmaceutically acceptable, water swellable polymer and an osmotic agent; and
(b) an outer coating layer which completely covers the osmotic core and comprises a pH sensitive coating agent and a water insoluble polymer. Optional coatings or seal coatings may additionally be applied. Delivery systems similar to this have been described in U.S. Pat. No. 5,916,595 and which is incorporated by reference.

In another embodiment, the present invention comprises a once a day controlled release medicament which comprises:

(a) a homogeneous compressed core of granules produced in a fluidized bed, said core comprising:
  (i) a medicament selected from a coated aspirin along with omeprazole;
  (ii) a water soluble osmotic compound;
  (iii) one or more osmotic polymers wherein one of the osmotic polymers is a water swellable osmotic polymer; and
(b) a membrane coating around said homogeneous compressed core. Delivery systems of this nature are described in U.S. Pat. No. 5,837,379 which is hereby incorporated by reference.

In yet another embodiment of the claimed invention, the present invention comprises a once-a-day aspirin/omeprazole delivery system for the treatment and prevention of heart attacks that comprises:

(a) from 20 to 50 wt. % of enteric polymeric membrane coated pellets comprising a polymer membrane coated core which comprises a biologically inert core which is coated with a first layer that comprises aspirin and a polymeric binder; and a second layer that comprises a membrane comprising a polymeric enteric coating material; and
(b) from 50 to 80 wt. % of delayed pulse polymer membrane coated pellets comprising a polymeric membrane coated core which comprises a biologically inert core which is coated with a combined first layer which comprises omeprazole and a polymeric binder polymer and a second layer which comprises a polymeric membrane that is permeable to omeprazole; and (c) a unit dose containment system. Delivery systems of this nature are described in U.S. Pat. No. 5,834,023 which is hereby incorporated by reference.

In one embodiment, the present invention also comprises a controlled release formulation which comprises:

(a) a core element comprising a compressed tablet which comprises a therapeutic dose of a combination of coated aspirin and omeprazole and an optional amount of a solubility modulating substance that is sufficient to control the release of said aspirin/omeprazole to provide a therapeutic level over a period of about 24 hours and;

(b) a sufficient amount of a substantially uniform enteric coating. This dosage form is generally described in U.S. Pat. No. 5,830,503 which is hereby incorporated by reference.

The solubility modulating substance is preferably dibasic sodium phosphate, but it is possible to use other solubility modulating agents such as sodium chloride, tribasic sodium phosphate, hydrogel forming polymers, such as hydroxypropyl methylcellulose, hydroxypropyl cellulose, hydroxyethyl cellulose, sodium alginate, xanthan gum, carbomer, and the like. In addition other pharmaceutically acceptable diluents such as lactose, dextrose, sucrose, starch, microcrystalline cellulose, dicalcium phosphate and the like.

The present invention also relates to a controlled release pharmaceutical tablet comprising:

(a) a compressed core which comprises:
  (i) a medicament selected from the combination of a anti-thrombotically effective amount of aspirin and omeprazole;
  (ii) at least 23% to 55% by weight, based on the total weight of the core, of a water soluble osmotic agent;
  (iii) a water soluble pharmaceutically acceptable polymeric binder;
  (iv) a water-swellable pharmaceutically acceptable polymer;
  (v) a conventional pharmaceutical excipient; and (b) a membrane coating comprising:
  (i) a modified water insoluble pharmaceutically acceptable polymer; and
  (ii) a pharmaceutically acceptable water soluble polymer. This system is described in U.S. Pat. No. 5,736,159 which is hereby incorporated by reference.

The present invention further relates to a controlled release pharmaceutical unit dose composition for oral administration comprising:

(a) an internal phase which comprises a coated aspirin in combination with a pharmaceutically effective amount of omeprazole in admixture with a hydrogel forming agent; and (b) an external phase which comprises a coating which resists dissolution in the stomach. This system is generally described in U.S. Pat. No. 5,728,402 which is hereby incorporated by reference.

Additionally, the present invention comprises a controlled release pharmaceutical tablet having at least one passageway, said tablet comprising:

(a) a compressed core that comprises:
  (i) a combination of a therapeutically effective amount of coated aspirin and omeprazole;
  (ii) an amount of a water soluble osmotic agent which is effective to cause the combination to be delivered from said passageway in the presence of aqueous media;
  (iii) a water-swellable pharmaceutically acceptable polymer; and (b) a membrane coating comprising a water insoluble pharmaceutically acceptable polymer. This system is generally described in U.S. Pat. No. 5,654,005 which is hereby incorporated by reference.

The present invention also relates to a controlled release medication comprising:

(a) a compressed core which comprises:
  (i) a combination of coated aspirin and omeprazole or aspirin as the active in the core or omeprazole as the active in the core;
  (ii) from 5 to 20 wt. % of a water soluble osmotic agent based upon the total weight of the core;
  (iii) a water soluble pharmaceutically acceptable polymeric binder;
  (iv) (iv) a conventional pharmaceutical excipient; and (b) a dual layer membrane coating around said core which comprises:
  (i) a first inner coating layer for sustained release of the medicaments, said inner coating layer comprising a plasticized water insoluble pharmaceutically acceptable polymer and a pharmaceutically acceptable water soluble polymer, and;
  (ii) a second outer coating layer for immediate release of a medicament, said outer coating layer optionally comprising an effective amount of aspirin or omeprazole and having a water soluble polymer. This system is generally described in U.S. Pat. No. 5,558,879 which is hereby incorporated by reference.

The present invention comprises a controlled release dosage pharmaceutical tablet which comprises:

(a) an osmotic core which comprises a coated aspirin and omeprazole and a water swellable component selected from the group consisting of hydroxypropylmethyl cellulose and a polyethylene oxide in admixture with the coated aspirin and omeprazole;

(b) a coating which comprises a water resistant polymer and a minor amount of a non-toxic, water soluble, pharmaceutically acceptable compound in an amount which is sufficient to dissolve in gastrointestinal fluid and form a plurality of micropores in the outside of said table, said water resistant polymer which are microporous to the passage of gastrointestinal fluid. This system is generally described in U.S. Pat. No. 5,458,887 which is hereby incorporated by reference.

A preferred delivery system comprises a novel dosage form which comprises:

(a) a compressed tablet core made from a granulation comprising a therapeutically effective amount of omeprazole and a coated aspirin; a surface active agent; a filler; a pharmaceutically acceptable alkaline agent; and a binder and (b) a layer of coating on said core.

The most preferred system comprises a dosage form having a pellet having an active core component selected from omeprazole that is coated with a granulation comprising omeprazole; a surface active agent; an alkaline material and a binder along with an optional filler. This active core component, in the preferred embodiment, is then coated onto an inert sphere to form to form the pellet. Before an enteric coating is applied, the sugar sphere or inert core is also coated with coated particles of aspirin to form a pellet having both omeprazole and aspirin on the pellet in either a single layer (if the omeprazole coated particles are blended with the coated aspirin particles before applying to the sugar sphere) or two layers in any order. The preferred order in a multi-layered pellet is to have the omeprazole layer as the outer layer adjacent to the enteric coating that is applied to form the enteric coated pellets. The enteric-coated pellets are then formed into capsules or tablets. The aspirin layer is preferably adjacent to the sugar sphere to permit slow release of the aspirin while taking advantage of the buffering effect and therapeutic effect of the omeprazole.

The inert component of the core may comprise a starch or sugar sphere such as non-pareil sugar seeds having an average size of from 14 to 35 mesh, preferably about 18–20 mesh. The core having inert component is coated with a formulation which comprises omeprazole and aspirin or formulations which comprise aspirin and which comprise omeprazole in a multi-layer system. The omeprazole formulation comprises an active core of omeprazole that is coated with an active omeprazole granulation formulation comprising omeprazole, a surface active agent, an alkaline material, a binder and optional fillers. This active omeprazole granulation formulation combined with the active core of omeprazole is hereinafter referred to as drug layer composition A. The aspirin formulation comprises an active core of aspirin that is coated with any coating that prevents direct contact of the aspirin with the omeprazole and which permits release of the aspirin to achieve the desired therapeutic effect of treating or preventing heart attacks or associated cardiovascular disorders.

Alternatively, and because of the acid protecting effect of the coating surrounding the active omeprazole core-the drug layer composition A-uncoated aspirin combination may also be applied directly to the sugar sphere either as a mixture combined with the drug layer composition A or as a separate layer when it is combined with the suitable excipients to form a drug layer composition B (e.g. with aspirin as the active ingredient in layer B). These excipients may be selected from similar ingredients to those in drug layer composition A except there is no need to have the alkaline material, although it may be added as well.

Thus, the inert central sugar sphere may be coated with a blend of drug layer composition A also containing aspirin or, the sugar sphere may be coated with drug layer composition A and drug layer composition B to form, after enteric coating, the delayed release pellets of the invention. These delayed release pellets are then formed into capsules or tablets.

The core forming inert component is employed at 1:1 to 5:1 and preferably from 2:1 to 3:1 weight ratio to the drug layer composition A also containing aspirin. Of course, this ratio varies depending upon the amount of omeprazole/aspirin that is added to the drug layer composition. The preferred dose of aspirin is in the 30–300 mgs per tablet range. One of skill in the art can vary the amount of omeprazole/aspirin to ensure that the ultimate tablet or capsule contains the target total milligrams of both active ingredients. Because platelet aggregation and the formation thereof vary on an individual basis, it may be necessary to prescribe different dosage regimes that are not dependent upon body weight alone.

For purposes of this invention, the omeprazole and the aspirin may collectively comprise from 20 to 70 wt. % and preferably 40 to 50 wt. % of the drug layer composition A plus aspirin. Or, if aspirin is in a separate layer B, the active ingredient aspirin also comprises 20 to 70 wt. % of the drug layer composition.

The surface active agent may be any pharmaceutically acceptable, non-toxic surfactant. Suitable surface active agents include sodium lauryl sulfate, polysorbate 20, polysorbate 40, polysorbate 60, polysorbate 80 and the like. This agent may be present at a level of from 0.1 to 5 wt. % and preferably 0.25 to 2.5 wt. % of drug layer composition A plus aspirin or drug layer A or B.

The alkaline material is selected from the group consisting of the sodium, potassium, calcium, magnesium and aluminum salts of phosphoric acid, carbonic acid, citric acid and aluminum/magnesium compounds such as $Al_2O_3.6MgO.CO_2.12H_2O$, $(Mg_6Al_2(OH_{1-6}CO_3.4H_2O)$, $MgO.Al_2O_3.2SiO_2.nH_2O$ where n is a whole integer of 2 or more. In addition the alkaline material may be selected from the group consisting of antacid materials such as aluminum hydroxides, calcium hydroxides, magnesium hydroxides and magnesium oxide. The alkaline agent may be present at a level of 1 to 20 wt % based on the total weight of the coating composition, depending on the relative strength of the alkaline material. If the preferred disodium phosphate alkaline agent is employed, a level of from 1 to 10 wt % and preferably 4 to 7 wt % based on the weight of the drug layer composition may be employed.

The binder may be any pharmaceutically acceptable, non-toxic pharmaceutically acceptable binder. The binder is preferably a water soluble polymer of the group consisting of polyvinyl alcohol, polyvinylpyrrolidone, methylcellulose, hydroxypropyl cellulose, hydroxymethyl cellulose and the like. A water soluble binder is preferred which is applied from an aqueous medium such as water at a level of from 0.1 to 5 wt % and preferably from 0.25 to 3 wt % of binder based on the total weight of the drug layer composition.

A filler is added to the drug layer. Sugars such as lactose, dextrose, sucrose, maltose, microcrystalline cellulose and the like may be used as fillers in the pellet coating composition. The filler may comprise from 20 to 70 wt % and preferably 40 to 50 wt % based on the total weight of the drug layer composition. In some formulations, the filler is not a critical component.

The enteric coating agent may comprise an acid resisting material which resists acid up to a pH of above about 5.0 or higher (e.g. between 5 and about 7) which is selected from the group consisting of cellulose acetate phthalate, hydroxypropylmethyl cellulose phthalate, polyvinyl acetate phthalate, carboxymethylethylcellulose, Eudragit L (poly(methacrylic acid, methylmethacrylate), 1:1 ratio; MW (No. Av. 135,000-USP Type A) or Eudragit S (poly(methacrylic acid, methylmethacrylate, 1:2 ratio MW (No. Av. 135,000-USP Type B) and mixtures thereof.

The enteric coating agent may also include an inert processing aid in an amount from 10 to 80 wt % and preferably 30 to 50 wt % based on the total weight of the acid resisting component and the inert processing aid. The inert processing aids include finely divided forms of talc, silicon dioxide, magnesium stearate etc. Typical solvents which may be used to apply the acid resisting component-inert processing aid mixture include isopropyl alcohol, acetone, methylene chloride and the like. Generally the acid resistant component-inert processing aid mixture will be applied from a 5 to 20 wt % of acid resisting component-inert processsing aid mixture based on the total weight of the solvent and the acid resistant component-inert processing aid.

The cores are formed by spraying the non-pareil seeds with an aqueous or non-aqueous suspension which contains the alkaline agent, the omeprazole, the surface active agent and the binder. The suspension medium may comprise any low viscosity solvent such as water, isopropyl alcohol, acetone, ethanol or the like. When fluids such as water are employed, this will usually require a weight of fluid which is about seven times the weight of the dry components of the coating composition. Alternatively, the cores are also formed by first coating a subparticle of omeprazole with an aqueous or non-aqueous suspension of a granulation comprising an alkaline agent, omeprazole, a surface active agent, an optional aspirin component and a binder. This formulation is then coated onto the non-pareil seeds to form an active core that is subsequently coated with an enteric coating or, before coating with the enteric coating, a layer B containing aspirin may be coated onto the first layer containing omeprazole (layer A) to form a multilayer system that is subsequently coated with an enteric coating.

After the cores are dried, the cores are coated with the enteric coating agent. A color imparting agent may be added to the enteric coating agent mixture or a rapidly dissolving seal coat containing color may be coated over the enteric coating agent layer provided that the seal coat is compatible with and does not affect the dissolution of the enteric coating layer.

The methods and compositions of the invention may be used prophylatically or therapeutically in the treatment of patients who are at risk or high risk of thrombus formation, such as in the treatment of atherosclerosis, vascular surgery patients, and patients with other types of cardiovascular disease. The therapeutic compositions of the invention comprising aspirin and omeprazole are utilized and are effective to reduce platelet aggregation over an extended period of time (12–24 hours) and also prevent or ameliorate the associated side effects (ulceration) of aspirin.

The composition of the invention can be administered in any effective pharmaceutically acceptable form to warm blooded animals including humans. These include oral, parenteral or infusable dosage forms, transdermal formulations or as a buccal or nasal spray. Routes of administration include intramuscular, intravenous, intraperitoneal or subcutaneous administration. Solid dosage forms for oral administration Include capsules, tablets, pills, powders and granules. These forms may additionally include inactive excipients including sugars, starches and the like and lubricating agents such as magnesium stearate. Buffering agents may also be included.

The term "omeprazole" also includes any pharmaceutically acceptable salt thereof and further includes stereoisomers including esoomeprazole (−) enantiomer of omeprazole and also the (+) stereoisomer. The omeprazole may be present as the acid addition salts or may be present as the sodium, magnesium, lithium or NR1R2 amine salt including the amino acids arginine and lysine.

Liquid dosage forms may also include emulsions, solutions, suspensions, syrups and elixers containing inert diluents commonly used in the art along with sweetening agents and the like.

EXAMPLE 1

Active pellets of omeprazole are formed by placing sugar spheres in a fluidized bed coater and spraying a suspension containing omeprazole and aspirin onto the sugar spheres. The formulation for making the active pellets has the following composition:

| | |
|---|---|
| povidone, USP (Plasdone K90) | 4.5 g |
| sodium lauryl sulfate, NF | 10.6 g |
| lactose anhydrous, NF | 427.7 g |
| disodium phosphate, NF | 51.3 g |
| omeprazole, USP (micronized) | 427.7 g |
| aspirin | 800.0 g |
| purified water, USP | 3336.0 g |

The povidone, lactose anhydrous, disodium phosphate and the purified water are mixed with a mechanical mixer until the materials are dissolved. Then the sodium lauryl sulfate is added to the mixture with gentle stirring to avoid the formation of excess foam until it dissolves completely. At that time the micronized omeprazole is added to the mixture and gentle stirring is continued until the micronized omeprazole is completely dispersed. Then, the aspirin (either coated or uncoated) is added to the blend.

2500.0 g of non-pareil sugar spheres (USPXII) (18/20 mesh) are placed in the fluidized bed coater and the suspension containing the omeprazole is coated at a product temperature of 35–45 degrees C.; an atomization pressure of 1.5–3.0 bar and a pump rate of 2–50 mL/minute, starting with a slow rate of pumping to avoid agglomeration and increasing the rate of pumping consistent with the avoidance of the formation of agglomerates.

After coating is complete the pellets are dried at a temperature of 50° C. until the loss on drying is less than 2.5 wt % The pellets are then screened through a #14 mesh screen and coated with the following enteric coating formulation:

| | |
|---|---|
| hydroxypropylmethylcellulose phthalate, NF | 258.1 g |
| cetyl alcohol, NF | 12.9 g |
| talc, USP | 129.0 g |
| isopropyl alcohol, USP* | 1663.0 g |
| acetone, NF* | 1663.0 g |

*evaporates during processing

The hydroxypropylmethylcellulose phthalate and the cetyl alcohol are mixed with the isopropyl alcohol and the acetone with agitation until all of the materials are dissolved. The talc is dispersed with agitation in this solution. One kilogram of the active pellets are placed in a fluidized bed coater and all of the enteric coating mixture is applied using the coating conditions that were used to form the active pellets. The enteric coated pellets are then placed into No."2", hard gelatin capsules containing pellets which are equivalent to 20 mg of omeprazole and 40 mg aspirin.

The capsules can be evaluated for stability as follows:

Dissolution stability:

After acid treatment for 2 hours in 500 ml of 0.1N HCl solution at 37° C., the test samples are tested according to the USP XXII dissolution test (type 1, basket) at 100 rpm, at 37° in phosphate buffer medium, USP XXII, at pH 6.8 to determine the percent of the drug dissolved versus time.

Chemical and Acid Resistance Stability:

The acid resistance study is conducted by using the USP XXII dissolution test (type 1, basket), 100 rpm, 37° C. in an aqueous solution of hydrochloric acid at pH 1.0.

All of the components, which are used in the present invention, are used in amounts that are effective for the intended purpose for which the component is employed.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A sustained release formulation comprising:
   (a) a plurality of particles, each of said particles comprising an inert core coated wit a first layer comprising omeprazole, aspirin, a surfactant, a binder, and an alkaline material; and
   (b) an enteric coating surrounding each of said coated particles.

2. The formulation according to claim 1 in the form of a tablet.

3. The formulation according to claim 1 in the form of a capsule.

4. A stable pharmaceutical composition of omeprazole and aspirin for oral administration comprising:
   a plurality of pellets comprising
   (a) an inert core component,
   (b) a first coating layer comprising omeprazole coated on said inert core component,
   (c) a second coating layer comprising aspirin coated onto said first coating layer,
   (d) an enteric coating layer comprising an enteric coating agent, said enteric coating agent surrounding said second coating layer,
   said pharmaceutical composition further comprising a surface active agent, a filler, a pharmaceutically acceptable alkaline agent and a binder.

5. The pharmaceutical composition of omeprazole as defined in claim 4 wherein the alkaline material is selected from the group consisting of the sodium, potassium, calcium, magnesium and aluminum salts of phosphoric acid, carbonic acid and citric acid.

6. The pharmaceutical composition of omeprazole as defined in claim 4 wherein the alkaline material is selected from the group consisting of the aluminum hydroxides, calcium hydroxides, magnesium hydroxides and magnesium oxide.

7. The pharmaceutical composition of omeprazole as defined in claim 4 wherein the enteric coating agent is selected from the group consisting of cellulose acetate phthalate, hydroxypropylmethyl cellulose phthalate, polyvinyl acetate phthalate, carboxymethylethylcellulose, co-polymerized methacrylic acid/methacrylic acid methyl esters.

8. The pharmaceutical composition of omeprazole as defined in claim 4 wherein the enteric coating agent also includes an inert processing aid.

9. The pharmaceutical composition of omeprazole as defined in claim 4 which includes a sodium lauryl sulfate as the surface active agent.

10. The pharmaceutical composition as defined in claim 4 wherein the core contains a non-pareil sugar seed.

11. The pharmaceutical composition of claim 4, wherein said surface active agent, said pharmaceutically acceptable alkaline agent and said binder are included in said second layer.

12. A controlled release formulation comprising:
    a plurality of pellets comprising,
    (a) an inert core component,
    (b) a first coating layer comprising a therapeutically effective amount of omeprazole coated on said inert core component,
    (c) a second coating layer comprising a therapeutically effective amount of aspirin coated onto said first coating layer,
    (d) an enteric coating layer comprising an enteric coating agent said enteric coating agent surrounding said second coating layer,
    said pharmaceutical composition further comprising a surface active agent, a filler, a pharmaceutically acceptable alkaline agent and a binder and said formulation effective to reduce platelet aggregation over a period of from 12 to 21 hours.

13. The controlled release formulation of claim 12, wherein said inert core component comprises non-pareil sugar seeds.

14. A controlled release formulation comprising:
    a plurality of pellets comprising,
    (a) an inert core component,
    (b) a first coating layer comprising a therapeutically effective amount of aspirin coated on said inert core component,
    (c) a second coating layer comprising a therapeutically effective amount of omeprazole coated onto said first coating layer,
    (d) an enteric coating layer comprising an enteric coating agent said enteric coating agent surrounding said second coating layer,
    said pharmaceutical composition further comprising a surface active agent, a filler, a pharmaceutically acceptable alkaline agent and a binder and said formulation effective to reduce platelet aggregation over a period of from 12 to 21 hours.

15. The controlled release formulation of claim 12, wherein said inert core component comprises non-pareil sugar seeds.

16. A stable pharmaceutical composition of omeprazole and aspirin for oral administration comprising:
    a plurality of pellets comprising
    (a) an inert core component,
    (b) a first coating layer comprising aspirin coated on said inert core component,
    (c) a second coating layer comprising omeprazole coated onto said first coating layer,
    (d) an enteric coating layer comprising an enteric coating agent, said enteric coating agent surrounding said second coating layer,
    said pharmaceutical composition further comprising a surface active agent a filler, a pharmaceutically acceptable alkaline agent and a binder.

* * * * *